United States Patent [19]

Gauthier

[11] Patent Number: 4,666,483
[45] Date of Patent: May 19, 1987

[54] METHOD AND INSTALLATION FOR RECOVERING THE HEAVIEST HYDROCARBONS FROM A GASEOUS MIXTURE

[75] Inventor: Pierre Gauthier, Fresnes, France

[73] Assignee: L'Air Liquide, Societe Anonyme pour l'Etude et l'Exploitation des Procedes George Claude, Paris, France

[21] Appl. No.: 769,628

[22] PCT Filed: Dec. 26, 1984

[86] PCT No.: PCT/FR84/00303
§ 371 Date: Aug. 14, 1985
§ 102(e) Date: Aug. 14, 1985

[87] PCT Pub. No.: WO85/03072
PCT Pub. Date: Jul. 18, 1985

[30] Foreign Application Priority Data

Dec. 30, 1983 [FR] France ............................ 83 21062

[51] Int. Cl.$^4$ ................................................ F25J 3/02
[52] U.S. Cl. .......................................... 62/24; 62/27; 62/38; 62/42
[58] Field of Search .................. 62/11, 20, 23, 24, 27, 62/32, 42, 34, 38; 55/46, 45; 208/340, 358, 365

[56] References Cited

U.S. PATENT DOCUMENTS

| | | | |
|---|---|---|---|
| 3,373,574 | 3/1968 | Fisher | 62/23 |
| 3,397,138 | 8/1968 | Bacon | 208/340 |
| 3,595,782 | 7/1971 | Bucklin et al. | 62/23 |
| 3,721,098 | 3/1973 | Forg et al. | 62/11 |
| 3,747,359 | 7/1973 | Streich | 62/11 |
| 4,242,875 | 1/1981 | Schaefer | 62/11 |
| 4,285,917 | 8/1981 | Knight | 62/11 |
| 4,404,008 | 9/1983 | Rentler et al. | 62/11 |

FOREIGN PATENT DOCUMENTS 2932561 2/1981 Fed. Rep. of Germany .

Primary Examiner—Ronald C. Capossela
Attorney, Agent, or Firm—Young & Thompson

[57] ABSTRACT

The gas to be treated is cooled and partly condensed in two steps (3-4, 5-6), and the condensed fractions are distilled in a column (9). A part of the condensed liquid at the top of the column is subcooled in the second exchanger 5, expanded, and vaporized in counter-current to the gas to be treated. This permits the obtainment of cooling temperatures on the order of −80° C. by means of a refrigerating unit (13, 20) operating at a temperature on the order of −30° to −40° C. Application to the recovery of a mixture of propane, butane and pentane from a petroleum refinery residual gas.

20 Claims, 1 Drawing Figure

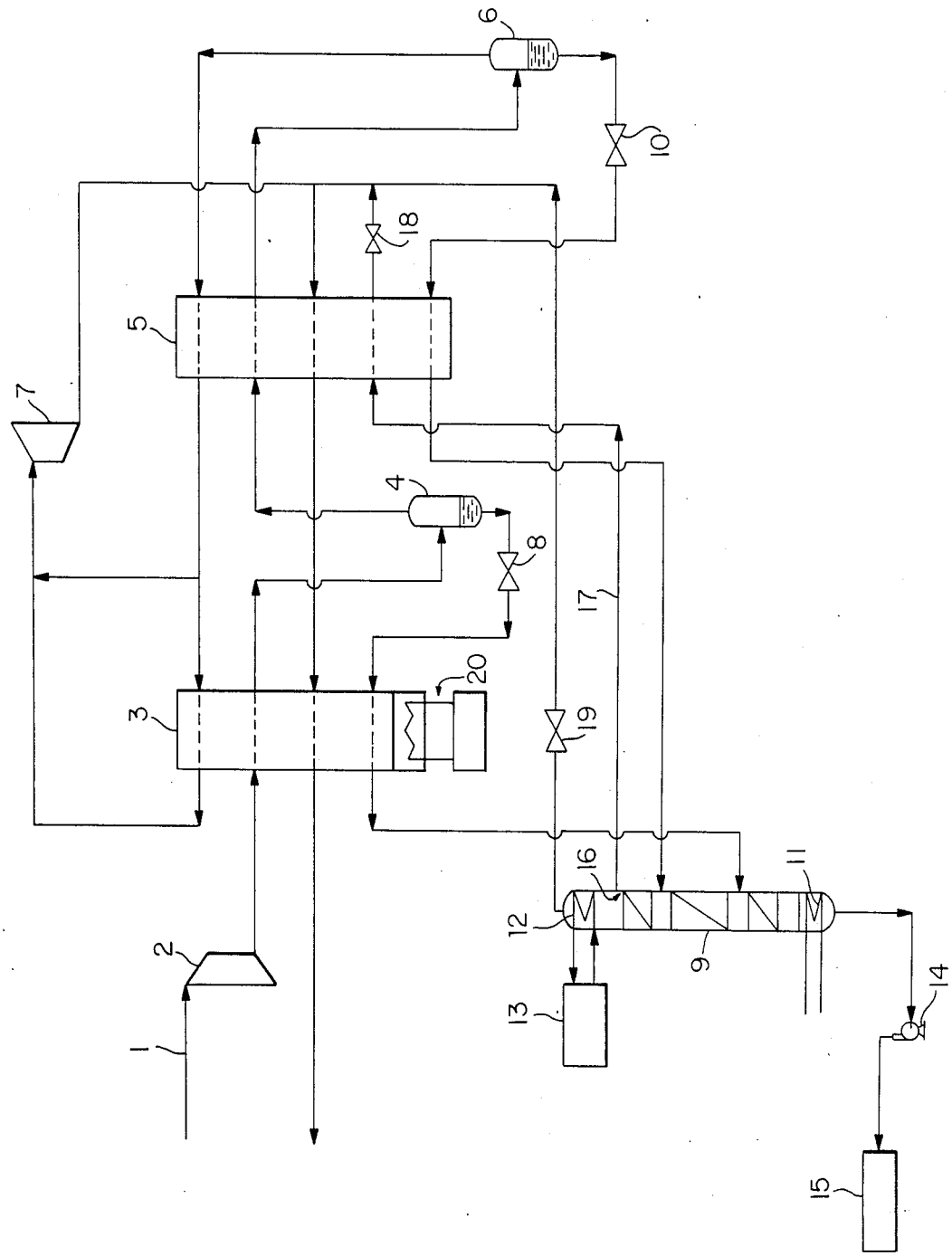

METHOD AND INSTALLATION FOR RECOVERING THE HEAVIEST HYDROCARBONS FROM A GASEOUS MIXTURE

The present invention relates to a method for recovering the heaviest hydrocarbons from a gaseous mixture, and in a particular to the recovery of a mixture of propane, butane and pentane from a petroleum refinery residual gas, of the type in which the gas to be treated is cooled and partly condensed and the condensate is distilled.

The mixtures of propane, butane and pentane, which are usually termed liquified petroleum gases or LPG, are condensed at ambient temperature under a pressure on the order of 10 to 20 bars. Their recovery from petroleum refinery residual gases is a recent development dictated by economic factors.

In the petroleum refinery residual gases, the LPG are diluted with lighter constituents, such as ethane, methane or hydrogen. It is usually necessary to remove these light constituents from these gases to a predetermined extent before sending them to a LPG treating unit which separates the constituents therefrom by distillation. This is why the recovery method itself includes a distillation operation.

In order to achieve a good propane, butane and pentane extraction yield, such a recovery method requires a cooling of the residual gas to a temperature on the order of −80° C. Now, the obtainment of this temperature level by the use of a refrigerating unit involves the use of complex refrigerating units having two stages and employing a vaporization under a vacuum, which presents outlay and working problems.

An object of the present invention is to provide a method whereby it is possible to obtain an extraction yield on the same order in a particularly simple and cheap manner.

The invention therefore provides a method of the aforementioned type which comprises vaporizing in counter-current heat exchange with the gas to be treated a part of the liquid condensed at the top of the distillation column.

In advantageous manners of carrying out the invention:

the liquid condensed at the top of the column is subcooled to the final temperature for cooling the gas to be treated and it is expanded before being vaporized;

there is combined with said expanded liquid the vapour at the top of the column expanded at the same pressure and/or the vapour issuing from the cooled gas to be treated, after having caused the latter to be circulated in counter-current to this gas and having expanded it in a turbine.

Another object of the invention is to provide an installation for carrying out such a method. This installation, which is of the type comprising a thermal exchange line provided with means for separating the condensate from the cooled gas, and a distillation column in which this condensate is introduced, is characterized in that the distillation column comprises means for recovering a part of the condensed liquid at the top of the column and means or circulating the recovered liquid in counter-current heat exchange with the gas in the thermal exchange line.

One example of carrying out the invention will now be described with reference to the accompanying drawing, the single FIGURE of which diagrammatically represents an installation for recovering LPG according to the invention.

The gas to be treated, which is conveyed by a conduit 1, is a petroleum refinery residual gas consisting of a mixture of C1 to C5 hydrocarbons and hydrogen. The purpose of the treatment is to eliminate almost completely the light constituents (C1 and C2 hydrocarbons and hydrogen) from this mixture. All the pressures mentioned hereinunder are absolute pressures.

The gas, which is compressed at 23 bars, 30° C. in a compressor 2, is cooled to an intermediate temperature on the order of −30° C. and partly condensed in a heat exchanger 3, and then divided into a liquid phase and a vapour phase in a phase separator 4. The vapour phase is cooled to about −82° C. in a second heat exchanger 5 and then divided into a liquid phase and a vapour phase in a second phase separator 6.

The vapour leaving the separator 6, which is almost solely formed by ethane, methane and hydrogen, is sent in counter-current to the exchanger 5; a part of this current is deviated to a turbine 7 while the remainder travels in counter-current through the exchanger 3 and then is also sent to this turbine. The gas expanded to 6 bars in the turbine 7 travels through the exchangers 5 and 3 in counter-current and constitutes a part of the residual gas of the recovery installation.

The liquid fraction issuing from the separator 4 is expanded in an expansion valve 8, passes in counter-current to the exchanger 3 and is then introduced in a distillation column 9 which is maintained at a pressure of 17 bars. Likewise, the liquid fraction issuing from the separator 6 is expanded in an expansion valve 10, travels in counter-current through the exchanger 5 and is then introduced in the column 9 at a level higher than that corresponding to the other liquid fraction.

The column 9 is provided, at the bottom, with a heat exchanger 11 employed for heating and in which circulates a heating fluid which may be steam at a pressure in the neighbourhood of the atmospheric pressure, and, at the top, with a condensing heat exchanger 12 connected to a refrigerating unit 13, for example employing ammonia or "Freon" providing a cooling effect at −33° C. The liquid at the bottom of the column 9, compressed to 25 bars by a pump 14, is sent to a storage tank 15 for subsequent treatment; it consists of a mixture of propane, butane and pentane from which have been removed to a predetermined extent lighter constituents and which for example contains ethane in a proportion lower than 2%.

A part of the liquid condensed by the condenser 12, consisting essentially of ethane and methane, is recovered by a trough 16 and sent through a conduit 17 to the exchanger 5, in which it is subcooled. At the cold end of this exchanger, this liquid is expanded to 6 bars in an expansion valve 18 and combined with the gaseous stream issuing from the turbine 7. Likewise, the vapour of the top of the column 2, essentially consisting, in the same way as the liquid condensed by the condenser 12, of ethane and methane, is expanded to 6 bars in an expansion valve 19 and then combined, at the cold end of the exchanger 5, with the gaseous stream issuing from the turbine 7. Thus, the whole of the turbined gaseous stream and the streams expanded in the valve 18 and 19 passes in counter-current through the exchangers 5 and then 3 so as to produce cold and then constitute the residual gas of the recovery installation.

It will therefore be understood that the installation described hereinbefore permits the obtainment of the temperature level of −80° C. required for a good extraction yield of LPG with the use of a simple refrigerating unit having a stage operating around −30° to −40° C.

Preferably, the refrigerating power at −33° C. required for the operation of the installation is divided between the top of the column 9 and the exchanger 3. This has been illustrated in the drawing by combining with this exchanger a second refrigerating unit 20. In fact, in practice, the installation has a single refrigerating unit a part of the refrigerating fluid of which travels through the exchanger 12 at the top of the column whereas another part is sent to the counter-current passages of the exchanger 3.

Two distinct heat exchangers 3 and 5 are shown in the drawing. In practice, there may be advantageously employed a single heat exchanger of the type having brazed plates provided with the necessary fluid inlets and outlets.

It will be understood that the same principle of transfer of cold at a lower temperature level by the liquid of the top of the distillation column may be applied to other types of recoveries of hydrocarbon mixtures having a number of carbon atoms at least equal to a given number, from a gaseous mixture containing, apart from these hydrocarbons, more volatile constituents.

What is claimed is:

1. A method for recovering a mixture of propane, butane and pentane from a gas further comprising lighter components including ethane, the method comprising cooling the gas to be treated to a low temperature so as to partly condense the gas, removing said lighter components from the condensate by distilling it under superatmospheric pressure in a distillation column, cooling the top of said column to a second temperature substantially higher than said low temperature thereby to condense liquid at the top of the column, withdrawing from said column liquid condensed at the top of the column, modifying said withdrawn liquid to bring it to a condition in which it boils at said low temperature, and vaporizing the modified liquid in counter-current heat exchange with the gas to be treated.

2. A method for recovering a mixture of propane, butane and pentane from a gas further comprising lighter components including ethane, the method comprising cooling the gas to be treated to a low temperature so as to partly condense the gas, removing said lighter components from the condensate by distilling it under superatmospheric pressure in a distillation column, cooling the top of said column to a second temperature substantially higher than said low temperature thereby to condense liquid at the top of the column, withdrawing from said column liquid condensed at the top of the column, expanding the withdrawn liquid and vaporizing said expanded liquid in counter-current heat exchange with the gas to be treated.

3. A method according to claim 2, comprising subcooling said withdrawn liquid to said low temperature before expanding it.

4. A method according to claim 2, comprising combining said withdrawn liquid with a first vapor issuing from said cooled gas prior to performing said vaporizing step.

5. A method according to claim 4, comprising circulating said first vapor in counter-current heat exchange to the gas to be treated and expanding said first vapor in a turbine prior to performing said combined step.

6. A method according to claim 2, comprising combining a second vapor withdrawn from the top of said column with said liquid prior to performing said vaporizing step.

7. A method for recovering a mixture of propane, butane and pentane from a gas further comprising lighter components including ethane, the method comprising cooling the gas to be treated to a low temperature so as to partly condense the gas, removing said lighter components from the condensate by distilling it under superatmospheric pressure in a distillation column, cooling the top of said column to a second temperature substantially higher than said low temperature thereby to condense liquid at the top of the column, withdrawing from said column liquid condensed at the top of the column, combining said withdrawn liquid with a first vapor issuing from said cooled gas so as to form a mixture which boils at said low temperature, and circulating said mixture in counter-current heat exchange with the gas to be treated.

8. A method as claimed in claim 7, comprising expanding said withdrawn liquid and said first vapor to a common low pressure before combining them.

9. A method according to claim 7, comprising subcooling said withdrawn liquid to said low temperature before combining it with said first vapor.

10. A method according to claim 7, comprising circulating said first vapor in counter-current heat exchange to the gas to be treated and expanding said first vapor in a turbine prior to performing said combining step.

11. An installation for recovering a mixture of propane, butane and pentane from a gas further comprising lighter components including ethane, comprising a thermal exchange line provided at a cold end thereof with a separator for separating into a condensate and a first vapor the cooled gas to be treated, means for heating said condensate in said thermal exchange line, and a superatmospheric distillation column in which said condensate is introduced after being heated in said thermal exchange line, the distillation column comprising a top condenser and means for maintaining the condenser at a second temperature substantially higher than said low temperature, means for withdrawing from the column liquid condensed at the top of the column, means for modifying said withdrawn liquid to bring it to a condition in which it boils at said low temperature, and means for vaporizing said modified liquid in said thermal exchange line in counter-current heat exchange with the gas to be treated.

12. An installation according to claim 11, further including means for subcooling said withdrawn liquid to said low temperature before expanding it.

13. An installation for recovering a mixture of propane, butane and pentane from a gas further comprising lighter components including ethane, comprising a thermal exchange line provided at a cold end thereof with a separator for separating into a condensate and a first vapor the cooled gas to be treated, means for heating said condensate in said thermal exchange line, and a superatmospheric distillation column in which said condensate is introduced after being heated in said thermal exchange line, the distillation column comprising a top condenser and means for maintaining the condenser at a second temperature substantially higher than said low temperature, means for withdrawing from the column liquid condensed at the top of the column, means for expanding the withdrawn liquid and means for vaporizing said expanded liquid in said thermal exchange line in counter-current heat exchange with the gas to be treated.

14. An installation according to claim 13, further including means for combining said withdrawn liquid with a first vapor issuing from said cooled gas prior to performing said vaporizing.

15. An installation according to claim 14, further including means for circulating said first vapor in counter-current heat exchange to the gas to be treated, and a turbine for expanding said first vapor prior to performing said combining step.

16. An installation according to claim 13, further including means for combining a second vapor withdrawn from the top of said column with said liquid prior to performing said vaporizing.

17. An installation for recovering a mixture of propane, butane and pentane from a gas further comprising lighter components including ethane, comprising a thermal exchange line provided at a cold end thereof with a separator for separating into a condensate and a first vapor the cooled gas to be treated, means for heating said condensate in said thermal exchange line, and a superatmospheric distillation column in which said condensate is introduced after being heated in said thermal exchange line, the distillation column comprising a top condenser and means for maintaining the condenser at a second temperature substantially higher than said low temperature, means for withdrawing from the column liquid condensed at the top of the column, means for combining said withdrawn liquid with said first vapor to form a mixture which boils at said low temperature, and means for circulating said mixture in counter-current heat exchange with the gas to be treated in the thermal exchange line.

18. An installation according to claim 17, further including means for expanding said withdrawn liquid and said first vapor to a common low pressure before combining them.

19. An installation according to claim 17, further including means for subcooing said withdrawn liquid to said low temperature before combining it with said first vapor.

20. An installation according to claim 17, further including means for circulating said first vapor in counter-current heat exchange to the gas to be treated, and a turbine for expanding said first vapor prior to performing said combining.

* * * * *